US009820732B2

(12) United States Patent
West, Jr.

(10) Patent No.: US 9,820,732 B2
(45) Date of Patent: Nov. 21, 2017

(54) SUTURE ANCHORS AND ASSEMBLIES FOR ATTACHING SOFT TISSUE TO BONE

(71) Applicant: Hugh S. West, Jr., Sandy, UT (US)

(72) Inventor: Hugh S. West, Jr., Sandy, UT (US)

(73) Assignee: HS WEST INVESTMENTS, LLC, Sandy, UT (US)

( * ) Notice: Subject to any disclaimer, the term of this patent is extended or adjusted under 35 U.S.C. 154(b) by 174 days.

(21) Appl. No.: 14/075,771

(22) Filed: Nov. 8, 2013

(65) Prior Publication Data

US 2014/0074163 A1    Mar. 13, 2014

Related U.S. Application Data

(60) Continuation of application No. 13/616,623, filed on Sep. 14, 2012, now Pat. No. 9,402,618, which is a
(Continued)

(51) Int. Cl.
*A61B 17/04* (2006.01)
*A61B 17/86* (2006.01)

(52) U.S. Cl.
CPC ........ *A61B 17/0401* (2013.01); *A61B 17/863* (2013.01); *A61B 2017/044* (2013.01); *A61B 2017/0414* (2013.01)

(58) Field of Classification Search
CPC .............. A61B 17/0401; A61B 17/863; A61B 2017/0414; A61B 2017/044; A61B 2017/0409; A61B 2017/0411; A61B 2017/0466; A61B 2017/0448; A61B 2017/045; A61B 2017/0451;
(Continued)

(56) References Cited

U.S. PATENT DOCUMENTS 2,243,717 A    5/1941    Godoy
2,489,870 A   11/1949    William
(Continued)

FOREIGN PATENT DOCUMENTS

EP    0705572    5/1995
EP    1584296    4/2005
(Continued)

OTHER PUBLICATIONS

U.S. Appl. No. 10/873,987, Apr. 17, 2007, Office Action.
(Continued)

*Primary Examiner* — Corrine McDermott
*Assistant Examiner* — Tin Nguyen
(74) *Attorney, Agent, or Firm* — Workman Nydegger (57) ABSTRACT

Improved bone anchors are disclosed for anchoring one or more sutures attached to soft tissue to a bone. The bone anchor has an anchor body that extends between a distal end and a proximal end. A bore is formed axially in the anchor body and opens at the proximal end. One or more pins are fixed within the bore of the anchor body. One or more sutures can be looped on the pins for anchoring soft tissue to bone. The anchor body has a socket within the bore for receiving a driver tool. The distal end of the anchor body forms a non-threaded extension, which stabilizes the bone anchor, and helps prevent lateral movement during use. In one embodiment, the anchor body has coarse threads for engaging soft bone tissue and fine threads for engaging hard bone tissue.

68 Claims, 3 Drawing Sheets

Related U.S. Application Data continuation of application No. 13/297,913, filed on Nov. 16, 2011, now Pat. No. 9,161,748, which is a division of application No. 11/317,204, filed on Dec. 22, 2005, now Pat. No. 8,114,127, which is a continuation-in-part of application No. 10/873,987, filed on Jun. 22, 2004, now Pat. No. 7,322,978.

(58) Field of Classification Search
CPC .... A61B 2017/0453; A61B 2017/0456; A61B 2017/0464; A61B 17/8645; A61B 17/864; A61F 2/0811
USPC ..... 623/13.14; 606/232, 300, 301, 303, 304, 606/305, 308
See application file for complete search history.

(56) References Cited

U.S. PATENT DOCUMENTS

| | | | |
|---|---|---|---|
| 3,861,269 A | 1/1975 | Laverty | |
| 4,590,928 A | 5/1986 | Hunt et al. | |
| 4,632,100 A | 12/1986 | Somers et al. | |
| 4,772,286 A | 9/1988 | Goble et al. | |
| 5,002,550 A | 3/1991 | Li | |
| 5,019,079 A | 5/1991 | Ross | |
| 5,156,616 A | 10/1992 | Meadows et al. | |
| D331,463 S | 12/1992 | Rosenberg | |
| 5,236,445 A | 8/1993 | Hayhurst et al. | |
| 5,370,662 A | 12/1994 | Stone et al. | |
| 5,411,506 A | 5/1995 | Goble et al. | |
| 5,411,523 A | 5/1995 | Goble | |
| 5,458,601 A | 10/1995 | Young, Jr. et al. | |
| 5,470,334 A | 11/1995 | Ross et al. | |
| 5,505,736 A | 4/1996 | Reimels et al. | |
| 5,571,139 A * | 11/1996 | Jenkins, Jr. ........ | A61B 17/0401 606/232 |
| 5,573,547 A | 11/1996 | LeVeen et al. | |
| 5,573,548 A | 11/1996 | Nazre et al. | |
| 5,575,801 A | 11/1996 | Habermeyer et al. | |
| 5,584,835 A | 12/1996 | Greenfield | |
| 5,591,207 A | 1/1997 | Coleman | |
| 5,690,676 A | 11/1997 | DiPoto et al. | |
| 5,694,783 A | 12/1997 | Bartlett | |
| 5,702,397 A | 12/1997 | Goble et al. | |
| 5,733,307 A | 3/1998 | Dinsdale | |
| 5,743,914 A | 4/1998 | Skiba | |
| 5,814,070 A | 9/1998 | Borzone et al. | |
| 5,824,011 A | 10/1998 | Stone et al. | |
| 5,851,219 A | 12/1998 | Goble et al. | |
| 5,868,789 A | 2/1999 | Huebner | |
| 5,891,168 A | 4/1999 | Thal | |
| 5,895,351 A | 4/1999 | Nottage et al. | |
| 5,904,704 A | 5/1999 | Goble et al. | |
| 5,911,721 A | 6/1999 | Nicholson et al. | |
| 5,935,129 A | 8/1999 | McDevitt et al. | |
| 5,957,953 A | 9/1999 | DiPoto et al. | |
| 5,961,524 A | 10/1999 | Crombie | |
| 5,964,783 A | 10/1999 | Grafton et al. | |
| 6,027,523 A | 2/2000 | Schmieding | |
| 6,045,573 A | 4/2000 | Wenstrom, Jr. et al. | |
| 6,096,060 A | 8/2000 | Fitts et al. | |
| 6,123,711 A | 9/2000 | Winters | |
| 6,139,565 A | 10/2000 | Stone et al. | |
| 6,149,653 A | 11/2000 | Deslauriers | |
| 6,159,235 A | 12/2000 | Kim | |
| 6,214,031 B1 | 4/2001 | Schmieding et al. | |
| 6,264,677 B1 | 7/2001 | Simon et al. | |
| 6,283,973 B1 | 9/2001 | Hubbard et al. | |
| 6,319,270 B1 | 11/2001 | Grafton et al. | |
| 6,319,271 B1 | 11/2001 | Schwartz et al. | |
| 6,436,124 B1 | 8/2002 | Anderson et al. | |
| 6,464,706 B1 | 10/2002 | Winter et al. | |
| 6,508,830 B2 | 1/2003 | Steiner | |
| 6,511,499 B2 | 1/2003 | Schmieding et al. | |
| 6,547,564 B1 | 4/2003 | Hansson | |
| 6,554,852 B1 | 4/2003 | Oberlander | |
| 6,569,186 B1 | 5/2003 | Winters et al. | |
| 6,569,188 B2 | 5/2003 | Grafton et al. | |
| 6,610,080 B2 | 8/2003 | Morgan | |
| 6,616,665 B2 | 9/2003 | Grafton et al. | |
| 6,623,492 B1 | 9/2003 | Berube et al. | |
| 6,641,596 B1 | 11/2003 | Lizardi et al. | |
| 6,648,892 B2 * | 11/2003 | Martello ............ | A61B 17/0401 606/319 |
| 6,648,903 B1 | 11/2003 | Pierson | |
| 6,652,563 B2 | 11/2003 | Dreyfuss | |
| 6,660,023 B2 | 12/2003 | McDevitt et al. | |
| 6,666,877 B2 | 12/2003 | Morgan et al. | |
| 6,699,250 B1 | 3/2004 | Osterle et al. | |
| 6,716,234 B2 | 4/2004 | Grafton et al. | |
| 6,743,233 B1 | 6/2004 | Baldwin et al. | |
| 6,840,953 B2 | 1/2005 | Martinek | |
| 6,923,824 B2 | 8/2005 | Morgan et al. | |
| 7,090,690 B2 | 8/2006 | Foerster et al. | |
| 7,322,478 B2 | 1/2008 | Goto et al. | |
| 7,322,978 B2 | 1/2008 | West | |
| 7,588,587 B2 | 9/2009 | Barbieri et al. | |
| 8,114,127 B2 | 2/2012 | West | |
| 8,343,186 B2 * | 1/2013 | Dreyfuss et al. ............. | 606/232 |
| 8,623,052 B2 * | 1/2014 | Dreyfuss et al. ............. | 606/232 |
| 8,801,755 B2 * | 8/2014 | Dreyfuss ............ | A61B 17/0401 606/232 |
| 9,521,999 B2 | 12/2016 | Dreyfuss et al. | |
| 2001/0004694 A1 | 6/2001 | Carchidi et al. | |
| 2001/0037113 A1 | 11/2001 | Justin | |
| 2001/0053913 A1 | 12/2001 | Freedland | |
| 2002/0016594 A1 | 2/2002 | Schlapfer et al. | |
| 2002/0052629 A1 * | 5/2002 | Morgan et al. ............. | 606/232 |
| 2002/0120292 A1 * | 8/2002 | Morgan ............ | A61B 17/0401 606/232 |
| 2002/0128684 A1 | 9/2002 | Foerster | |
| 2002/0147463 A1 * | 10/2002 | Martinek ............ | 606/232 |
| 2002/0173822 A1 | 11/2002 | Justin et al. | |
| 2002/0183751 A1 | 12/2002 | Justin et al. | |
| 2003/0004545 A1 | 1/2003 | Burkhart et al. | |
| 2003/0065332 A1 | 4/2003 | TenHuisen et al. | |
| 2003/0065361 A1 | 4/2003 | Dreyfuss | |
| 2003/0074002 A1 | 4/2003 | West, Jr. | |
| 2003/0088252 A1 | 5/2003 | Kaikkonen et al. | |
| 2003/0125745 A1 | 7/2003 | Tseng et al. | |
| 2003/0144696 A1 | 7/2003 | Sinnott et al. | |
| 2003/0158555 A1 | 8/2003 | Sanders et al. | |
| 2003/0187446 A1 | 10/2003 | Overaker et al. | |
| 2003/0187477 A1 | 10/2003 | Lintner | |
| 2003/0204193 A1 | 10/2003 | Gabriel et al. | |
| 2004/0030354 A1 | 2/2004 | Leung et al. | |
| 2004/0106950 A1 | 6/2004 | Grafton et al. | |
| 2004/0133239 A1 | 7/2004 | Singhatat | |
| 2005/0119698 A1 | 6/2005 | Martinek | |
| 2005/0222618 A1 * | 10/2005 | Dreyfuss ............ | A61B 17/0401 606/232 |
| 2005/0283158 A1 | 12/2005 | West | |
| 2006/0100630 A1 | 5/2006 | West | |
| 2012/0065677 A1 | 3/2012 | West | |
| 2012/0143250 A1 | 6/2012 | West | |
| 2013/0013064 A1 | 1/2013 | West | |

FOREIGN PATENT DOCUMENTS

| | | |
|---|---|---|
| EP | 1588666 | 4/2005 |
| EP | 1260182 | 11/2007 |
| JP | 10-507398 | 8/1998 |
| WO | 97/06731 | 2/1997 |
| WO | 00/69532 | 11/2000 |
| WO | 02/11630 | 2/2002 |
| WO | 2004/047617 | 6/2004 |
| WO | 2005/102190 | 3/2005 |

OTHER PUBLICATIONS

U.S. Appl. No. 10/873,987, Sep. 20, 2007, Notice of Allowance.
U.S. Appl. No. 11/317,204, Jan. 21, 2010, Office Action.
U.S. Appl. No. 11/317,204, May 6, 2010, Office Action.

(56) References Cited

OTHER PUBLICATIONS

U.S. Appl. No. 11/317,204, Dec. 8, 2010, Office Action.
U.S. Appl. No. 11/317,204, Apr. 6, 2011, Office Action.
U.S. Appl. No. 11/317,204, Jun. 24, 2011, Office Action.
U.S. Appl. No. 11/317,204, Oct. 24, 2011, Notice of Allowance.
Office Action cited in U.S. Appl. No. 13/297,913, dated May 14, 2014.
Office Action cited in U.S. Appl. No. 13/351,460, dated Apr. 9, 2014.
Office Action cited in U.S. Appl. No. 13/616,623, dated Mar. 27, 2014.
Barber, F.A., et al., Sutures and Suture Anchors: Update 2003, *Arthroscopy: The Journal of Arthroscopic and Related Surgery*, vol. 19, No. 9 Nov. 2003: pp. 985-990.
Barber, F.A., et al., Sutures and Suture Anchors—Update 2006, *Arthroscopy: The Journal of Arthroscopic and Related Surgery*, vol. 22, No. 10 Oct. 2006: pp. 1063-1069.
The American Heritage College Dictionary, 2000, 3$^{rd}$ Edition, Exhibit pp. 1-11, Houghton Mifflin Company, USA (11 pgs).
Barber et al., "Suture Anchor Failure Strength—An In Vivo Study", Arthroscopy: The Journal of Arthroscopic and Related Surgery, 1993, 9(6): 647-652, Raven Press. Ltd., North America.
Barber et al., "The Ultimate Strength of Suture Anchors", Arthroscopy: The Journal of Arthroscopic and Related Surgery, vol. 11, No. 1 Feb. 1995: pp. 21-28.
Barber et al., "Suture Anchor Strength Revisited", Arthroscopy: The Journal of Arthroscopic and Related Surgery, vol. 12, No. 1 Feb. 1996: pp. 32-38.
Barber et al., "Internal Fixation Strength of Suture Anchors—Update 1997", Arthroscopy: The Journal of Arthroscopic and Related Surgery, vol. 13, No. 3 Jun. 1997: pp. 355-362.
Barber et al., "Suture Anchors—Update 1999", Arthroscopy: The Journal of Arthroscopic and Related Surgery, vol. 15, No. 7 Oct. 1999: pp. 719-725.
Barber et al., "Sutures and Suture Anchors: Update 2003", Arthroscopy: The Journal of Arthroscopic and Related Surgery, vol. 19, No. 9 Nov. 2003: pp. 985-990.
Burkhart et al., "Cyclic Loading of Anchor-Based Rotator Cuff Repairs: Confirmation of the Tension Overload Phenomenon and Comparison of Suture Anchor Fixation With Transosseous Fixation" Arthroscopy: The Journal of Arthroscopic and Related Surgery, vol. 13, No. 6 Dec. 1997: pp. 720-724.
The Chambers Dictionary, 2003, Exhibit pp. 1-5, Chambers Harrap Publishes Ltd., Edinburgh, UK (5 pgs).
Curriculum Vitae of Mark A. Ritchart (3 pgs).
Declaration of Mark A. Ritchart—*Smith & Nephew, Inc. & Arthrocare Corporation v. Arthrex, Inc.* (313 pgs).
Ex Parte Dreyfuss, et al., No. 2013-000360 (PTAB Jul. 23, 2015) (8 pgs).
Goble et al., "The Development of Suture Anchors for Use in Soft Tissue Fixation to Bone" The American Journal of Sports Medicine, 1994, pp. 236-239, vol. 22, No. 2, American Orthopaedic Society for Sports Medicine.
Goradia et al., "Cyclic Loading of Rotator Cuff Repairs: A Comparison of Bioabsorbable Tacks with Metal Suture Anchors and Transosseous Sutures", Arthroscopy: The Journal of Arthroscopic and Related Surgery, vol. 17, No. 4 Apr. 2001: pp. 360-364.
Hecker et al., "Pull-out strength of suture anchors for rotator cuff and Bankart lesion repairs", The American Journal of Sports Medicine, 1993, pp. 874-879, vol. 21, No. 6, American Orthopaedic Society for Sports Medicine.
Lajtai et al., "Chapter 4—Suture Anchors—Shoulder Arthroscopy and MRI Techniques", 2003, pp. 47-58, Springer-Verlag, New York.
The Merriam-Webster Dictionary, 2004, 31$^{st}$ Printing, Exhibit pp. 1-5, Quad Graphics, Martinsburg, WV (5 pgs).
Petition for *Inter Partes* Review, *Smith & Nephew, Inc. & Arthrocare Corporation v. Arthrex, Inc.*, U.S. Pat. No. 8,343,186, IPR No. 2016-00505 (69 pgs).
Petition for *Inter Partes* Review, *Smith & Nephew, Inc. & Arthrocare Corporation v. Arthrex, Inc.*, U.S. Pat. No. 8,623,052, IPR No. 2016-00506 (69 pgs).
Petition for *Inter Partes* Review, *Smith & Nephew, Inc. & Arthrocare Corporation v. Arthrex, Inc.*, U.S. Pat. No. 8,801,755, IPR No. 2016-00507 (70 pgs).
Petition for *Inter Partes* Review, *Smith & Nephew, Inc. & Arthrocare Corporation v. Arthrex, Inc.*, U.S. Pat. No. 8,801,755, IPR No. 2016-00508 (70 pgs).
Rupp et al., "Fatigue Testing of Suture Anchors", The American Journal of Sports Medicine, 2002, pp. 239-247, vol. 30, No. 2, American Orthopaedic Society for Sports Medicine.
U.S. Food and Drug Administration, "Use of International Standard ISO-10993, 'Biological Evaluation of Medical Devices Part 1: Evaluation and Testing' (Replaces #G87-1 #8294) (blue book memo)(Text Only)", Jan. 13, 2016, pp. 1-9, http://www.fda.gov/RegulatoryInformation/Guidances/ucm080735.htm 9 pgs).
Webster's Third New International Dictionary of the English Language Unabridged, 1993, Exhibit pp. 1-4, Merriam-Webster Inc., Publishers, Springfield, Massachusetts (4 pgs).
U.S. Appl. No. 13/297,913, Sep. 12, 2014, Final Office Action.
U.S. Appl. No. 13/616,623, Sep. 12, 2014, Final Office Action.
U.S. Appl. No. 13/351,460, Oct. 1, 2014, Final Office Action.
U.S. Appl. No. 13/351,460, May 22, 2015, Office Action.
U.S. Appl. No. 13/297,913, Aug. 28, 2015, Notice of Allowance.
U.S. Appl. No. 13/616,623, Jun. 9, 2015, Office Action.
U.S. Appl. No. 13/616,623, Oct. 7, 2015, Notice of Allowance.
U.S. Appl. No. 13/351,460, Oct. 15, 2015, Final Office Action.

\* cited by examiner

SUTURE ANCHORS AND ASSEMBLIES FOR ATTACHING SOFT TISSUE TO BONE

RELATED APPLICATION

This application is a continuation of U.S. patent application Ser. No. 13/616,623, filed Sep. 14, 2012, which is a continuation of U.S. patent application Ser. No. 13/297,913, filed Nov. 16, 2011, which is a division of U.S. patent application Ser. No. 11/317,204, filed Dec. 22, 2005, now issued U.S. Pat. No. 8,114,127, which is a continuation-in-part of U.S. patent application Ser. No. 10/873,987, filed Jun. 22, 2004, now issued U.S. Pat. No. 7,322,978, the disclosures of which are incorporated herein in their entirety.

BACKGROUND OF THE INVENTION

1. The Field of the Invention

The present invention relates to soft tissue repair surgery, such as rotator cuff repair surgery. More specifically, the present invention relates to a bone anchor used to attach soft tissue to bone using a suture.

2. Related Technology

Soft tissue injuries, especially rotator cuff injuries, can occur from repeated stress or acute trauma. The rotator cuff is a group of muscles and tendons in the shoulder that attach to the humerus bone of the arm. The rotator cuff allows a person to rotate the arm and raise it above the head. A common injury to the rotator cuff occurs when repeated stress or acute trauma causes the rotator cuff to partially or completely tear away from the humerus bone. These and similar types of injuries may require surgery to correctly reattach the soft tissue to the bone.

Various devices have been used to reattach soft tissue to bone. Known methods include staples, wedges, plugs, screws, and sutures alone. Threaded suture anchors, such as bone screws, have recently been developed to provide a particularly firm location where a suture can be anchored to bone. In these systems, a suture is tied between the bone anchor and soft tissue. Providing a firm attachment point for the suture is important because of the relatively strong forces that are experienced in a flexing muscle.

Despite recent advances in bone anchors, existing bone anchors and rotator cuff repairs can fail and have other disadvantages. Typically, a rotator cuff repair fails either because the bone anchor dislodges or the suture tears through the soft tissue. As force is applied to the suture, the suture can cut through the soft tissue like a cheese wire, leaving the rotator cuff detached from the humerus bone. When one suture fails, it can place more stress on the surrounding sutures, thus increasing the likelihood that other sutures will fail in like manner.

Using a greater number of sutures per unit area of soft tissue can minimize suture attachment failure. However, the number of sutures is limited by the space available for inserting bone anchors. Alternatively, additional sutures can be connected to a single bone anchor. Double and triple loading of bone anchors, however, increases the forces applied to the bone anchor and increases the likelihood that the bone anchor will fail by being pulled out of the bone into which it is secured.

Bone anchors can fail for various reasons. One reason is that existing bone anchors are not threaded to the proximal end of the anchor where the anchor meets the surface of the bone in the hard cortical bone region. In existing bone screws, the proximal end is not threaded because the driver tool used to insert the bone anchor fits over a hex shaped protrusion. The hex protrusion cannot extend above the bone surface so the screw is driven into the bone until the protrusion is below the surface. Since the protrusion has no threads, the bone anchor does not engage the bone near the surface, but only the soft cancellous bone beneath the cortical bone layer. This feature of existing bone anchors is very problematic because it prevents a practitioner from placing the threads of the bone anchor in the harder cortical bone, which is near the bone surface.

Some existing anchors engage the sutures above the anchor threads. Such screws have an eyelet formed in the protrusion used to drive the screw. Sutures are looped in the eyelet and fed through the driver tool. Because the attachment point for the sutures is above the threads, the threaded portion of the bone anchor experiences a high torque moment when a force is applied by the suture to the attachment point. Consequently, existing bone anchors are prone to experience a certain degree of movement within the soft bone layer. In some cases, the bone anchor can retreat from the bone and rub against soft tissues overlaying the bone anchor. This may result in the irritation or damage of such tissues.

Recently, bone screws have been used that place the attachment point for the sutures within the body of the screw, specifically within the bore of the screw. In these screws an attachment site within the bore is created using a small piece of suture. The ends of the suture are fed through holes near the proximal end of the screw to form a small suture loop within the bore. Knots are tied in the end of the suture to prevent the ends from passing back though the holes. The suture loop within the bore provides an anchoring point for threading sutures used to secure tissue in a surgical procedure.

One problem with these screws is that the knots that hold the suture loop can come untied and/or break, which releases the sutures anchored to the suture loop. This problem is particularly difficult to fix once the screw has been placed in a patient because it would require the surgeon to remove the screw from the patient. An additional problem with using suture loops as an attachment mechanism is that the suture material can fray as the anchored sutures slide on it. Furthermore, when loading multiple sutures on the suture loop, the suture loop can flex and cause the sutures to bunch together. When a practitioner is using a suture the practitioner needs the suture to freely slide in the bone anchor. The friction and/or pinching that a suture loop can cause between lengths of suture can cause suture capture, which is undesirable.

Therefore, what is needed is a bone anchor that better engages its surrounding bone tissue and allows greater forces to be applied to the bone anchor without becoming dislodged or failing. In addition, a bone anchor is needed that can reduce suture capture.

BRIEF SUMMARY OF THE INVENTION

The bone anchors of the present invention overcome the disadvantages of the prior art discussed above by providing improved suture attachment sites and improved threads for engaging bone tissue. In an exemplary embodiment, the bone anchor of the present invention has an anchor body extending between a proximal end and a distal end. A continuous thread extends around the anchor body and is configured to engage both cortical and cancellous bone tissue. The anchor body includes an interior surface that defines a bore that opens at the proximal end of the anchor body. One or more transverse pins are placed in and across the bore interior to provide one or more locations within the interior of the anchor body for looping one or more sutures.

According to one embodiment, the pins are placed deep within the bore of the anchor body. This feature allows room for a socket to be formed in the proximal end of the anchor body where a driver tool can be inserted for driving the bone anchor into a bone. Because the driver tool is placed on the interior of the bone anchor, the anchor body can be threaded to the proximal end. Threading the proximal end of the anchor body provides the bone anchor with the ability to better engage the cortical bone near the surface of the bone.

The placement of the pins also provides a more central location for anchoring sutures. The more centrally anchored sutures exert a force on the anchor body that is more evenly distributed and more aligned with the axis of the bone anchor. Consequently, the bone anchor can better distribute the exerted force to the surrounding bone tissue without causing the bone tissue to weaken so as to cause loosening or withdrawal of the bone anchor.

The pins disposed within the bore of the anchor body also provide a better attachment mechanism for attaching a suture than exists in the prior art. The pins are securely fixed to the anchor body. Unlike the bone anchors in the prior art, the bone anchors of the present invention do not rely on knots to secure sutures within the bore. In addition, the pins are made of a material that does not fray and is less likely to break.

Double and triple loading of the bone anchor with more than one suture is more easily accomplished with a pin because the pins provide individual attachment locations for each additional suture. In one exemplary embodiment, two pins are disposed in the bore at right angles to each other. Two sutures are loaded on the lower pin with the upper pin separating the two sutures. In another embodiment, the upper pin is also loaded with a suture. This latter configuration properly spaces three sutures and minimizes friction and suture capture among the three sutures.

In an exemplary embodiment, the anchor body has a non-threaded portion at the distal end that forms a stabilizing extension. The extension provides additional stability to the bone anchor by reducing the tendency of the anchor body to move or rotate laterally. Bone anchors are often placed in a bone at an angle. Much like a longer tent stake is less likely to give out, the extension of the bone anchor of the present invention helps prevent the bone anchor from becoming dislodged. Stabilizing the bone anchor reduces the likelihood that the bone anchor will fail and allows the bone anchor to be safely loaded with more sutures.

In yet another embodiment, the anchor body is a screw that includes a portion of fine threads and a portion of coarse threads. The fine threads are configured to engage hard bone tissue, such as cortical bone, and the coarse threads are configured to engage soft bone tissue, such as cancellous bone. A portion of the threads are made finer by increasing the root diameter and increasing the surface angle of the thread. The pitch of the coarse threads and fine threads is kept the same such that the proximal threads can follow the impression created by the distal threads as the bone anchor is driven into a bone.

Optimizing the thread pattern for engaging different types of bone tissue allows the bone anchor to better engage adjacent bone tissue. Because the bone anchor can better engage adjacent bone tissue, the bone anchor can be loaded with additional sutures without compromising stability of the bone anchor. The additional sutures per anchor reduce the stress placed on each individual suture through the soft tissue, which helps prevent the sutures from cutting through the soft tissue.

These and other objects and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6B illustrates the bone anchor of FIG. 6A

DETAILED DESCRIPTION OF EXEMPLARY EMBODIMENTS

Figure 1:
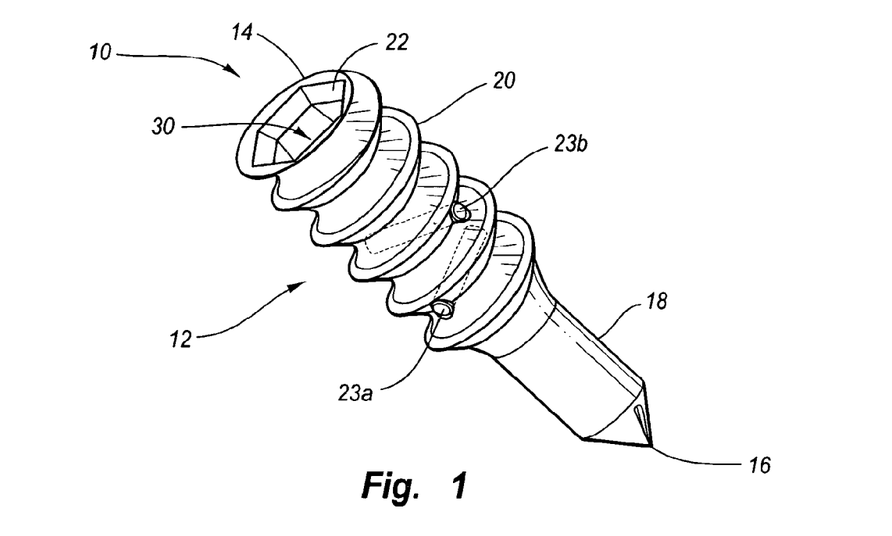
FIG. 1 is a perspective view of an exemplary bone anchor according to the invention.

With reference to FIG. 1, exemplary embodiments of the present invention are directed to an improved bone anchor 10 for affixing soft tissue to bone, such as in a rotator cuff repair surgery. Bone anchor 10 has an anchor body 12, which extends between a proximal end 14 and a distal end 16. Distal end 16 of anchor body 12 has a non-threaded portion that forms a stabilizing extension 18. Stabilizing extension 18 helps prevent lateral movement of anchor body 12 within bone tissue during use. Anchor body 12 further comprises a threaded portion, which includes threads 20 for engaging bone tissue.

Proximal end 14 includes an opening 30, which provides access to a hollow interior bore 30 of anchor body 12. A hex socket 22 is formed in bore 30 of anchor body 12, which allows bone anchor 10 to be driven into a bone using a hex driver. It will be appreciated that bore 30 of anchor body 12 can have any other desired shape, such as triangular, square, pentagonal, star-shaped, oval, etc. Transverse pins 23a and 23b are disposed through anchor body 12 and provide attachment points for looping sutures thereon.

Figure 2:
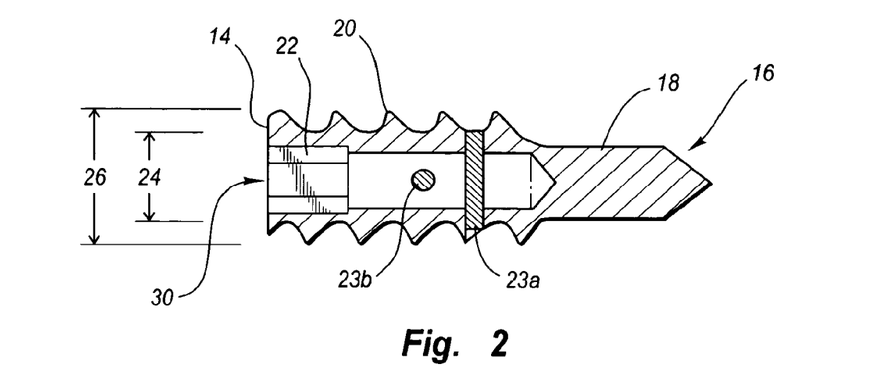
FIG. 2 is a cross-sectional view of the bone anchor of FIG. 1 showing a bore extending through the anchor body.

FIG. 2 illustrates a cross-sectional view of bone anchor 10. In an exemplary embodiment, anchor body 12 has a length of about 8 to about 15 mm, a major diameter 26 of about 5 mm, and a root diameter 24 of about 3.5 mm. Anchor body 12 can have sizes other than these; however, the size of anchor body 12 is limited by the size of the bone where the bone anchor 10 is to be placed. For example, in rotator cuff repair surgery, increasing the diameter of anchor body 12 can reduce the number of bone anchors 10 that can be positioned at the repair site.

Bone anchor 10 has threads 20 that wrap continuously around anchor body 12 in a desired (e.g., clockwise) direction. The pattern of threads 20 determines in part how bone anchor 10 engages surrounding bone tissue. In one embodiment, threads 20 make about six turns around anchor body 12 and extend toward proximal end 16.

As shown in FIG. 2, major diameter 26 and root diameter 24 may taper slightly inward toward distal end 16. The slight taper causes the threads 20 to engage bone tissue more tightly as the bone anchor 10 is driven further into a bone. Of course, bone anchor 10 can have threads that taper more or less depending on a practitioner's preference and/or the needs of a patient.

Anchor body 12 also has a non-threaded portion at distal end 16, which forms stabilizing extension 18. Stabilizing extension 18 is generally cylindrical and typically has a width less than root diameter 24. In one embodiment, the length of extension 18 is more than about 20% of the length of the threaded portion of anchor body 10. In another embodiment, extension 18 is more than 100% the length of the threaded portion and in yet another embodiment, more than about 200% of the length of the threaded portion.

In one embodiment, extension 18 is configured to be inserted into a pilot hole drilled into the bone where bone anchor 10 is to be placed. Preparing a pilot hole reduces the risk that insertion of the screw in a bone will cause damage to bone anchor 10 and/or fracture bone tissue as the bone anchor 10 is inserted into the bone. Preventing damage to bone anchor 10 and surrounding bone tissue reduces the chances that bone anchor 10 will become loosened or fail during use. In another embodiment, the bone anchor can have a self drilling distal end.

Anchor body 12 is advantageously made from a strong biocompatible material, such as a titanium alloy or stainless steel. Alternatively, anchor body 12 can be made from a biodegradable material, such as poly-l-lactic acid (PLLA) that can be absorbed into adjacent bone tissue over time as the repair site heals. Other biocompatible and/or biodegradable materials suitable for use in bone anchors are known to those skilled in the art.

Bore 30 opens at proximal end 14 to provide access to the interior of anchor body 12. In an exemplary embodiment, a proximal portion of bore 30 is hexagonally shaped to form a hex socket 22 for receiving a hex driver. This female type driver tool engagement mechanism eliminates the need to have a protruding proximal end 16. Instead, proximal end 16 is substantially flat and can be placed at or just below a bone surface, as discussed more fully below.

Figure 3:
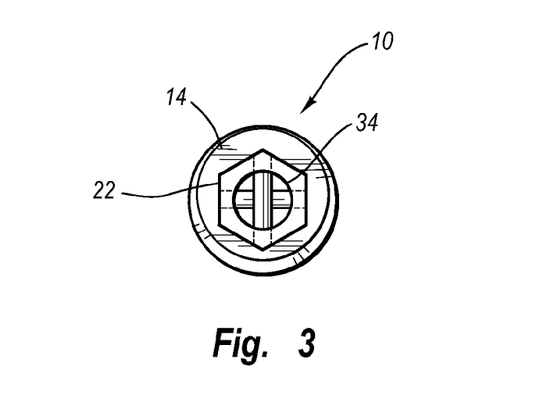
FIG. 3 is a proximal end view of the bone anchor of FIG. 1 showing a drive socket and two perpendicularly-arranged pins within the bore.

As shown in FIGS. 2 and 3, hex socket 22 can be wider than the distal portion of bore 30. For example, a ridge 34 can be formed at the distal end of hex socket 22. Ridge 34 acts as a stop to limit how deep a hex driver can be inserted therein (e.g., to protect post 23b and/or a suture attached thereto). Alternatively, the insertion depth of a hex driver can be controlled by placing a ridge of material on the hex driver. In this case, insertion of the driver would be stopped when the ridge on the driver engages the proximal end 16 of the anchor body 12.

The distal portion of bore 30 also contains one or more transverse pins for looping sutures thereon. Pins 23a and 23b are formed or inserted in anchor body 12 lying across bore 30. The diameter of pins 23a and 23b are selected such that there is sufficient space between pin 23a and pin 23b and interior surface 28 for passing a suture around the pins 23a and 23b. In addition to providing a location for looping sutures, pins 23a and 23b provide additional structural support (i.e., an endoskeleton) to anchor body 12.

Pins 23a and 23b are disposed in bore 30 substantially non-parallel to each other. As illustrated in FIG. 3, in one embodiment, pins 23a and 23b are at right angles to each other. Offsetting pins 23a and 23b exposes portions of pin 23a that would otherwise be occluded from the top by pin 23b. Such a configuration allows a suture to be loaded on pin 23a on either side of pin 23b, as shown in FIG. 4.

Figure 4:
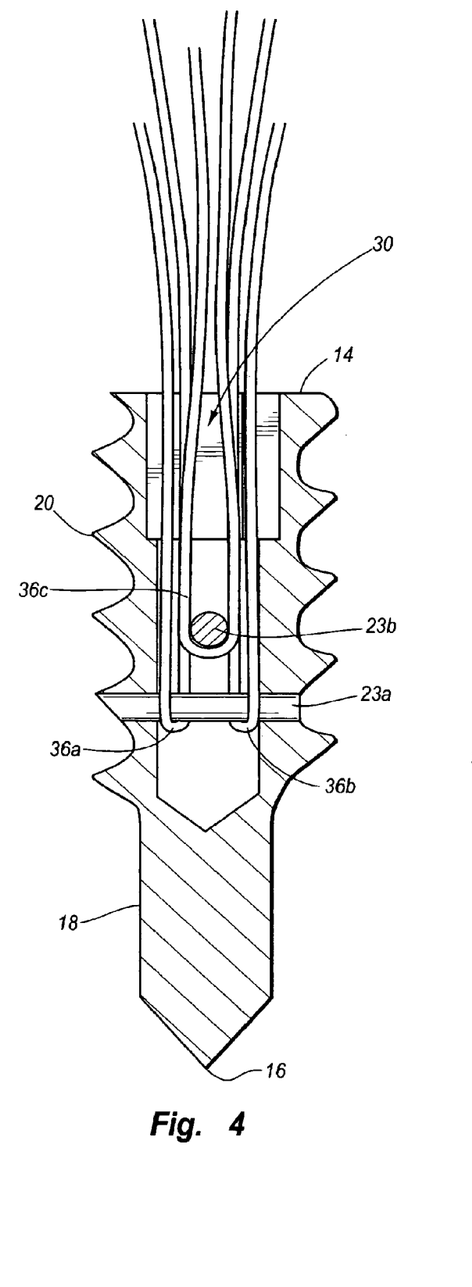
FIG. 4 is a cross-sectional view of the bone anchor of FIG. 1 with three sutures being looped around the two pins disposed in the bore.

Bone anchor 10, in FIG. 4, is illustrated loaded with three sutures 36a, 36b, and 36c (collectively sutures 36). Pin 23a is shown loaded with sutures 36a and 36b extending on either side of pin 23b. Pin 23b has a single suture 36c loaded thereon. Each suture has its own space to slide on its respective pin 23a or 23b. The proper spacing of sutures 36 in bone anchor 10 prevents sutures 36 from rubbing extensively or getting caught on one another.

Another advantageous feature of pins 23a and 23b is their position distal to hex socket 22 and within bore 30. Pins 23a and 23b are placed within bore 30 such that the forces applied by sutures 36 are transferred to a more central location within anchor body 12. Forces applied to bone anchor 10 below the surface of a bone are less likely to cause bone anchor 10 to become loosened or dislodged. Pins 23a and 23b are placed below hex socket 22 so a hex driver can be inserted without hitting the pins. This placement also allows sutures to be threaded through a hole in a driver tool (not shown) so that bone anchor 10 can be installed preloaded with sutures.

While bone anchor 10 has been illustrated with two pins (i.e., pins 23a and 23b), bone anchor 10 may have more or fewer pins depending on the required number of sutures and/or the space available within bore 30 for placing more sutures. For instance, in another embodiment, the anchor body 12 may have a single post with one or more sutures loaded thereon. Furthermore, a second pin can be disposed in bore 30 even where sutures are to be placed only on one pin, with the second pin being used solely to separate sutures. In addition, a second pin can be placed in anchor body 12 for structural support only.

Pins 23a and 23b are made from a strong metal or synthetic fiber so as to provide a rigid attachment point for sutures 36. In an exemplary embodiment, pins 23a and 23b are cylindrical to provide a smooth surface for sutures 36 to slide against. While pins 23a and 23b are illustrated as straight, pins 23a and 23b can be bent or have shapes other than cylindrical. Straight pins, however, can be more easily placed in anchor body 12 and therefore can reduce the cost and complexity of manufacturing bone anchor 10. The foregoing and similar attachment devices are examples of rigid attachment means for attaching a suture to an anchor.

In one embodiment, one or both of pins 23a and 23b are made from a radioopaque material such as titanium or stainless steel. A radioopaque pin can be used with a radiotransparent anchor body, such as an anchor body made from a biodegradable material such as PLLA. This configuration of materials allows a practitioner to identify and locate bone anchor 10 in a radiograph when bone anchor 10 is made mostly of biodegradable materials.

The bone anchor according to the present invention need not be formed as a threaded device, but can also be formed as a tap-in type anchor. Also, the measurements, angles and ratios between the dimensions of the bone anchor can be varied from those described above and in the following alternative embodiment so as to be suitable for the conditions and applications in which the bone anchor is to be used.

Figure 5A:
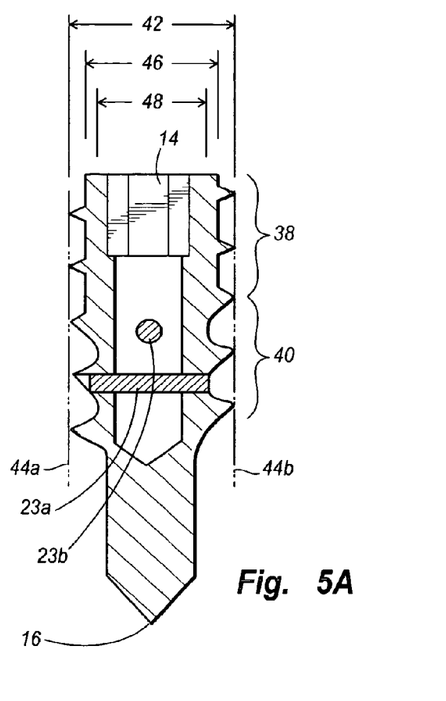
FIG. 5A illustrates an alternative embodiment of an exemplary bone anchor of the invention having finer proximal threads for engaging hard cortical bone and coarser distal threads for engaging soft cancellous bone.

FIG. 5A shows an alternative embodiment of the bone anchor of the present invention having a section of finer threads 38 at the proximal end 16 and a section of coarser threads 40 distal thereto. Fine threads 38 and coarse threads 40 have the same major diameter 42 which has a slight taper illustrated by lines 44a and 44b. Fine thread 38 and coarse threads 40, have different root diameters 46 and 48 respectively. Root diameters 46 and 48 have a slight taper similar to major diameter the taper shown by lines 44a and 44b.

Fine threads 38 are finer because they have a wider root diameter 46. Root diameter 46 of fine thread 38 is wider than root diameter 48 of coarse threads even after subtracting out the increase in width due to the overall taper of anchor body 12 as illustrated by lines 44a and 44b. Fine threads 38 have root diameter 46 and a major diameter 42 that are configured to engage harder bone. Coarse threads 40 have a root diameter 48 and major diameter 42 that are configured to engage soft bone. In an exemplary embodiment, major diameter 42 is about 5.3 mm, root diameter 46 is about 4.8 mm and root diameter 48 is about 3.3 mm. Fine threads 38 can have a similar shape as coarse threads 40 or a different shape as desired. For example, fine threads 38 can have a larger or smaller thread angle.

In one embodiment, fine threads 38 have the same pitch as coarse threads 40. By keeping the pitch the same between thread sections, the finer threads 38 will be able to use the same impression cut by coarse threads 40.

Figure 5B:
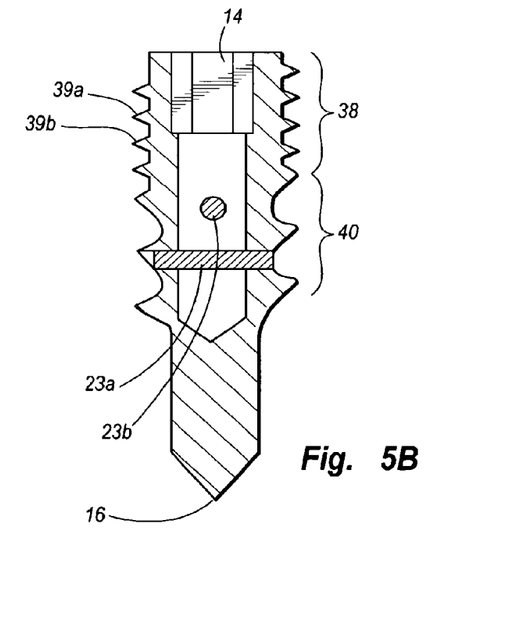
FIG. 5B illustrates the bone anchor of FIG. 5A with double flute thread on the cortical portion of the bone anchor.

FIG. 5B shows yet another alternative embodiment of the present invention where fine threads 38 form a double flute. A first flute 39a follows the thread pattern of coarse threads 40 such that first flute 39a follows the grooves created by coarse threads 40 as the bone anchor 10 is driven into a bone. In an exemplary embodiment, second flute 39b has the same pitch as first flute 39a. Second flute 39b can have a similar shape as flute 39a or a different shape as desired. For example, threads 39b can have a larger or smaller thread angle and/or major diameter.

Figure 6:
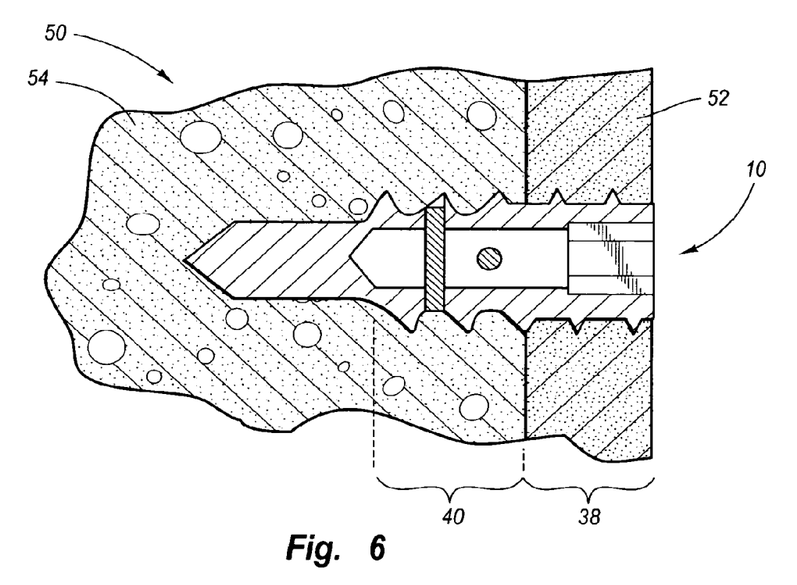
FIG. 6 illustrates the bone anchor of FIG. 5A placed within a bone such that the fine threads engage a hard cortical bone region and coarse threads engage a soft cancellous bone region.

FIG. 6 shows bone anchor 10 disposed in a typical bone 50 having a cortical bone region 52 and a cancellous bone region 54. Cortical bone region 52 comprises dense bone, while cancellous bone region 54 comprises bone that is soft or spongy. When bone anchor 10 is properly inserted into bone 50, fine threads 38 engage the hard cortical bone region 52 and coarse threads 40 engage the softer cancellous bone region 54.

In manufacturing bone anchor 10, in accordance with the present invention, anchor body 12 and posts 23 can be cast and formed in a die. Alternatively anchor body 12 can be cast or formed and posts 23a and 23b inserted later. For instance, anchor body 12 can be cast and formed from PLLA. Anchor body 12 can then be drilled to prepare holes for stainless steel pins 23a and 23b.

The suture anchors according to the present invent can be distributed to practitioners with one or more of sutures 36 threaded through bore 30 and looped to pins 23a and/or 23b. In one method of manufacturing bone anchor 10, sutures 36 are looped on pins 23a and 23b as pins 23a and 23b are inserted into anchor body 12.

An example of a type of suture suitable for use in conjunction with the bone anchor of the present invention is #2 braided polyester. If more than one strand of sutures 36 is used, the sutures can be a different color such that a practitioner can more easily pair the ends of the sutures during a surgical operation.

Figure 7:
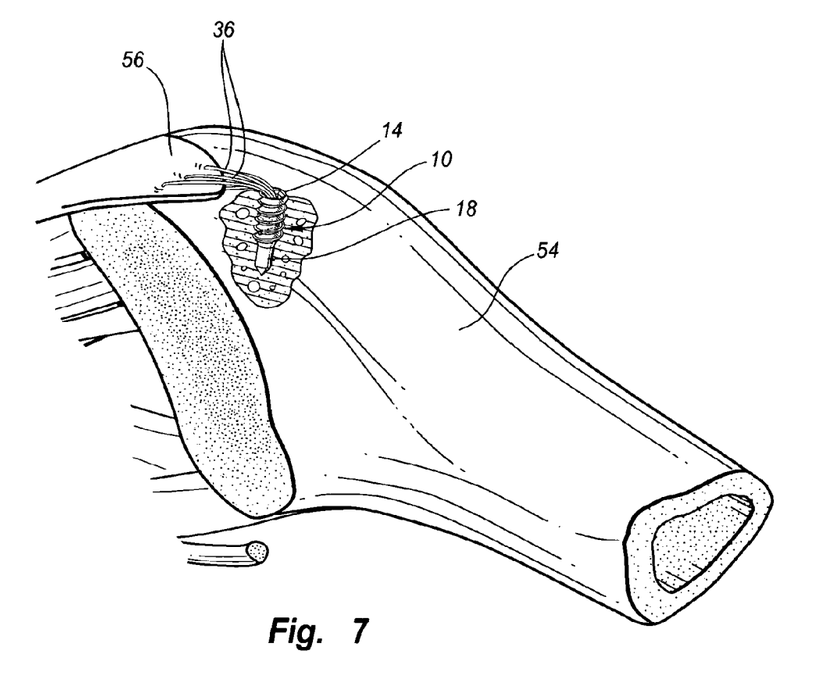
FIG. 7 illustrates an exemplary bone anchor of the invention placed in a humerus bone of a person with sutures attached to the bone anchoring being looped through and securing the person's rotator cuff.

FIG. 7 illustrates the use of bone anchor 10 in a rotator cuff repair surgery. Bone anchor 10 is placed in humerus bone 54, and sutures 36 are passed through rotator cuff 56 and tied. Before bone anchor 10 is inserted in humerus bone 54 a pilot hole may be drilled. Bone anchor 10 is inserted into the pilot hole using a driver tool until proximal end 14 is substantially flush with the outer surface of humerus bone 54. Bone anchor 10 is advantageously placed in humerus bone 54 at an angle to the tangent of the humerus bone, also known as the "dead man's angle."

Because bone anchor 10 is placed in humerus bone 54 at an angle, extension 18 provides a mechanical advantage against bone anchor 10 moving laterally and opening the angle to the tangent. By preventing lateral movement, extension 18 prevents sutures 36 from loosening once sutures 36 have been properly tied. In addition, if bone anchor 10 were to move within bone 54, bone anchor 10 can become dislodged and fail. Extension 18 does not have threads thereon, which reduce friction as bone anchor 10 is driven into a pilot hole.

Proximal end 14 of bone anchor 10 is substantially flat or non-protruding such that bone anchor 10 can be placed at or just below the surface of bone 54. Threads extend to proximal end 14 such that bone anchor 10 has maximum engagement with bone 54. The opening at proximal end 14 also allows for sutures 36 to exit the bore. The opening of the bore is smooth such that sutures 36 can easily slide thereon.

Sutures 36 exit bone anchor 10 at proximal end 14 and are drawn through the soft tissue of rotator cuff 56. Sutures 36 can be spaced to more evenly distribute the load exerted by rotator cuff 56. As shown in FIGS. 5 and 7, sutures 36 exert a force on bone anchor 10 on the pins in the bone and at proximal end 14. Because proximal end 14 is at or below the surface of bone 54, less torsion is applied to bone anchor 10. Instead, the force of rotator cuff 56 is distributed vertically along the anchor body through the pins. Consequently, bone anchor 10 is less likely to be dislodged and fail.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture anchor for attachment of tissue to bone, comprising:
  an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;
  at least one thread beginning at a periphery of the proximal face and extending distally toward the distal end to form a threaded portion of the anchor body, the threaded portion including a proximal threaded half and a distal threaded half;

a socket formed in the proximal bore portion and opening at the proximal face for receiving a correspondingly shaped driver; and a rigid member fixedly attached to the anchor body within the distal bore portion and distal to the socket, wherein the rigid member is transverse to the longitudinal axis and includes a proximal surface and a distal surface, wherein the rigid member, including the proximal surface and the distal surface, are fixedly positioned in a region of the anchor body containing the distal threaded half so as to provide a fixed location within the distal bore portion and in the region containing the distal threaded half for attachment of a suture loop.

2. The suture anchor of claim 1, wherein the socket has a hexagonal shape.

3. The suture anchor of claim 1, wherein the socket has a square shape.

4. The suture anchor of claim 1, wherein the socket has shape that is triangular, pentagonal, star-shaped, or oval.

5. The suture anchor of claim 1, wherein the distal bore portion is cylindrical.

6. The suture anchor of claim 5, wherein the distal bore portion has a constant uninterrupted diameter except where the rigid member is located.

7. The suture anchor of claim 1, wherein the proximal surface and the distal surface of the rigid member each extend laterally and inwardly from the interior surface of the anchor body defining the interior bore so as to be transverse to the longitudinal axis.

8. The suture anchor of claim 7, wherein the rigid member has a width defined by a distance between the proximal surface and the distal surface of the rigid member.

9. The suture anchor of claim 7, wherein the distal bore portion has a distal end region distal to the distal surface of the rigid member.

10. The suture anchor of claim 9, wherein the distal end region of the distal bore portion has the same diameter as a remaining portion of the distal bore portion between the proximal bore portion and the proximal surface of the rigid member.

11. The suture anchor of claim 7, further comprising a suture loop attached to the rigid member.

12. The suture anchor of claim 11, wherein a distal portion of the suture loop is adjacent to and abuts the distal surface of the rigid member and a proximal portion of the suture loop is proximal to the proximal surface of the rigid member.

13. The suture anchor of claim 1, further comprising a looped suture, a portion of which exits through the socket and extends outside the anchor body beyond the proximal face.

14. The suture anchor of claim 13, wherein the looped suture has free ends for attachment to soft tissue.

15. The suture anchor of claim 14, wherein the free ends are unattached to each other.

16. The suture anchor of claim 1, wherein the anchor body comprises stainless steel.

17. The suture anchor of claim 1, wherein the anchor body comprises a titanium alloy.

18. The suture anchor of claim 1, wherein the anchor body comprises a biodegradable material.

19. The suture anchor of claim 18, wherein the biodegradable material comprises poly-l-lactic acid.

20. The suture anchor of claim 1, wherein the anchor body is tapered.

21. The suture anchor of claim 1, wherein the threaded portion extends partially to the distal end of the anchor body.

22. The suture anchor of claim 21, wherein the anchor body further comprises a non-threaded portion at the distal end.

23. The suture anchor of claim 1, wherein the rigid member has an axis that is generally perpendicular to the longitudinal axis of the anchor body.

24. The suture anchor of claim 1, wherein the rigid member comprises a transverse pin extending across the distal bore portion.

25. The suture anchor of claim 1, wherein the rigid member includes a first side and a second side, and wherein the first and second sides are substantially aligned with the longitudinal axis of the anchor body.

26. A suture anchor assembly comprising:
the suture anchor of claim 1; and
a driver having a size and shape so as to be positionable within the socket of the suture anchor without hitting the rigid member.

27. The suture anchor assembly of claim 26, wherein the driver further includes a hole through which a suture, when attached to the suture anchor, can be threaded.

28. A suture anchor for attachment of tissue to bone, comprising:
an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;

at least one thread beginning at a periphery of the proximal face and extending distally toward the distal end to form a threaded portion of the anchor body, the threaded portion including a proximal threaded half and a distal threaded half;

a socket formed in the proximal bore portion and opening at the proximal face for receiving a correspondingly shaped driver;

a rigid member fixedly attached to the anchor body within the distal bore portion and distal to the socket, wherein the rigid member is transverse to the longitudinal axis and includes a proximal surface and a distal surface, wherein the rigid member, including the proximal surface and the distal surface, are fixedly positioned in a region of the anchor body containing the distal threaded half so as to provide a fixed location within the distal bore portion and in the region containing the distal threaded half for attachment of a suture loop; and a suture loop attached to the rigid member, wherein a distal end portion of the suture loops abuts the distal surface of the rigid member to restrict proximal movement of the suture loop with respect to the rigid member, and wherein a proximal portion of the suture loop is proximal to the proximal surface of the rigid member.

29. The suture anchor of claim 28, wherein the proximal surface and the distal surface of the rigid member each extend laterally and inwardly from the interior surface of the anchor body defining the interior bore so as to be transverse to the longitudinal axis.

30. The suture anchor of claim 28, wherein the distal bore portion has a distal end region distal to the distal surface of the rigid member.

31. The suture anchor of claim 30, wherein the distal end portion of suture loop is positioned within the distal end region of the distal bore portion.

32. The suture anchor of claim 30, wherein the distal end region of the distal bore portion has the same diameter as a remaining portion of the distal bore portion between the proximal bore portion and the proximal surface of the rigid member.

33. The suture anchor of claim 28, wherein the socket has a hexagonal shape.

34. The suture anchor of claim 28, wherein the socket has a square shape.

35. The suture anchor of claim 28, wherein the distal bore portion is cylindrical.

36. The suture anchor of claim 35, wherein the distal bore portion has a constant uninterrupted diameter except where the rigid member is located.

37. The suture anchor of claim 28, wherein the anchor body comprises stainless steel.

38. The suture anchor of claim 28, wherein the anchor body comprises a titanium alloy.

39. The suture anchor of claim 28, wherein the anchor body comprises a biodegradable material.

40. The suture anchor of claim 39, wherein the biodegradable material comprises poly-l-lactic acid.

41. The suture anchor of claim 28, wherein the anchor body is tapered.

42. The suture anchor of claim 28, wherein the threaded portion extends partially to the distal end of the anchor body.

43. The suture anchor of claim 42, wherein the anchor body further comprises a non-threaded portion at the distal end.

44. The suture anchor of claim 28, wherein the rigid member has an axis that is generally perpendicular to the longitudinal axis of the anchor body.

45. The suture anchor of claim 44, wherein the rigid member comprises a transverse pin extending across the distal bore portion.

46. A suture anchor assembly comprising:
the suture anchor of claim 28; and
a driver having a size and shape so as to be positionable within the socket of the suture anchor.

47. The suture anchor assembly of claim 46, wherein the driver includes a hole through which free ends of a looped suture can be threaded.

48. A suture anchor assembly for attachment of tissue to bone, comprising:
an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;
at least one thread beginning at a periphery of the proximal face and extending distally toward the distal end to form a threaded portion of the anchor body, the threaded portion including a proximal threaded half and a distal threaded half;
a socket formed in the proximal bore portion and opening at the proximal face for receiving a correspondingly shaped driver;
a rigid member fixedly attached to the anchor body within the distal bore portion and distal to the socket, wherein the rigid member is transverse to the longitudinal axis and includes a proximal surface and a distal surface, wherein the rigid member, including the proximal surface and the distal surface, are fixedly positioned in a region of the anchor body containing the distal threaded half so as to provide a fixed location within the distal bore portion and in the region containing the distal threaded half for attachment of a suture loop; and
a driver having a size and shape so as to be positionable within the socket of the anchor body without hitting the rigid member.

49. The suture anchor assembly of claim 48, wherein the proximal surface and the distal surface of the rigid member each extend laterally and inwardly from the interior surface of the anchor body defining the interior bore.

50. The suture anchor assembly of claim 48, wherein the distal bore portion has a distal end region distal to the distal surface of the rigid member.

51. The suture anchor assembly of claim 50, wherein the distal end region of the distal bore portion has the same diameter as a remaining portion of the distal bore portion between the proximal bore portion and the proximal surface of the rigid member.

52. The suture anchor assembly of claim 50, further comprising a suture loop attached to the rigid member, wherein a distal portion of the suture loop is adjacent to and abuts the distal surface of the rigid member to restrict proximal movement of the suture loop with respect to the rigid member, and wherein a proximal portion of the suture loop is proximal to the proximal surface of the rigid member.

53. The suture anchor assembly of claim 52, wherein the distal portion of suture loop is positioned within the distal end region of the distal bore portion.

54. The suture anchor assembly of claim 48, wherein the socket has a hexagonal shape.

55. The suture anchor assembly of claim 48, wherein the socket has a square shape.

56. The suture anchor assembly of claim 48, wherein the distal bore portion is cylindrical, and wherein the distal bore portion has a constant uninterrupted diameter except where the rigid member is located.

57. The suture anchor assembly of claim 48, wherein the anchor body comprises stainless steel.

58. The suture anchor assembly of claim 48, wherein the anchor body comprises a titanium alloy.

59. The suture anchor assembly of claim 48, wherein the anchor body comprises a biodegradable material.

60. The suture anchor assembly of claim 59, wherein the biodegradable material comprises poly-l-lactic acid.

61. The suture anchor assembly of claim 48, wherein the anchor body is tapered.

62. The suture anchor assembly of claim 48, wherein the threaded portion extends partially to the distal end of the anchor body.

63. The suture anchor assembly of claim 62, wherein the anchor body further comprises a non-threaded portion at the distal end.

64. The suture anchor assembly of claim 48, wherein the rigid member has an axis that is generally perpendicular to the longitudinal axis of the anchor body.

65. The suture anchor assembly of claim 64, wherein the rigid member comprises a transverse pin extending across the distal bore portion.

66. A suture anchor for attachment of tissue to bone, comprising:
an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;

at least one thread beginning at a periphery of the proximal face and extending distally toward the distal end to form a threaded portion of the anchor body, the threaded portion including a proximal threaded half and a distal threaded half;

a socket formed in the proximal bore portion and opening at the proximal face for receiving a correspondingly shaped driver; and a rigid member fixedly attached to the anchor body within the distal bore portion and distal to the socket, wherein the rigid member is transverse to the longitudinal axis and positioned in a region of the anchor body containing the distal threaded half so as to provide a fixed location within the distal bore portion and in the region containing the distal threaded half for attachment of a suture loop, wherein the rigid member has a proximal surface, a distal surface, and a width defined by a distance between the proximal surface and the distal surface, wherein the rigid member, including the proximal surface of the rigid member, is positioned distal to an intersection between the proximal threaded half and the distal threaded half, wherein the distal bore portion has a distal end region distal to the distal surface of the rigid member and which has the same diameter as a remaining portion of the distal bore portion between the proximal bore portion and the proximal surface of the rigid member.

67. A suture anchor for attachment of tissue to bone, comprising:

an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;

at least one thread beginning at a periphery of the proximal face and extending distally toward the distal end to form a threaded portion of the anchor body, the threaded portion including a proximal threaded half and a distal threaded half;

a socket formed in the proximal bore portion and opening at the proximal face for receiving a correspondingly shaped driver;

a rigid member fixedly attached to the anchor body within the distal bore portion and distal to the socket, wherein the rigid member is transverse to the longitudinal axis and positioned in a region of the anchor body containing the distal threaded half so as to provide a fixed location within the distal bore portion and in the region containing the distal threaded half for attachment of a suture loop; and a suture loop attached to the rigid member, wherein the rigid member has a proximal surface, a distal surface, and a width defined by a distance between the proximal surface and the distal surface, wherein the rigid member, including the proximal surface of the rigid member, is positioned distal to an intersection between the proximal threaded half and the distal threaded half, wherein the distal bore portion has a distal end region distal to the distal surface of the rigid member, wherein a portion of the suture loop is adjacent to and abuts the distal surface of the rigid member to restrict proximal movement of the suture loop with respect to the rigid member.

68. A suture anchor assembly for attachment of tissue to bone, comprising:

an anchor body having a longitudinal axis, a proximal end forming a proximal face transverse to the longitudinal axis, a distal end, and an interior surface which defines an interior bore that opens at the proximal face and extends distally from the proximal end along the longitudinal axis, the interior bore having a proximal bore portion and a distal bore portion;

at least one thread beginning at a periphery of the proximal face and extending distally toward the distal end to form a threaded portion of the anchor body, the threaded portion including a proximal threaded half and a distal threaded half;

a socket formed in the proximal bore portion and opening at the proximal face for receiving a correspondingly shaped driver;

a rigid member fixedly attached to the anchor body within the distal bore portion and distal to the socket, wherein the rigid member is transverse to the longitudinal axis and positioned in a region of the anchor body containing the distal threaded half so as to provide a fixed location within the distal bore portion and in the region containing the distal threaded half for attachment of a suture loop; and a driver having a size and shape so as to be positionable within the socket of the anchor body, wherein the rigid member has a proximal surface, a distal surface, and a width defined by a distance between the proximal surface and the distal surface, wherein the rigid member, including the proximal surface of the rigid member, is positioned distal to an intersection between the proximal threaded half and the distal threaded half, wherein the distal bore portion has a distal end region distal to the distal surface of the rigid member and which has the same diameter as a remaining portion of the distal bore portion between the proximal bore portion and the proximal surface of the rigid member.

* * * * *

UNITED STATES PATENT AND TRADEMARK OFFICE
CERTIFICATE OF CORRECTION

PATENT NO. : 9,820,732 B2
APPLICATION NO. : 14/075771
DATED : November 21, 2017
INVENTOR(S) : West, Jr.

It is certified that error appears in the above-identified patent and that said Letters Patent is hereby corrected as shown below:

On the Title Page

Item (56) References Cited, U.S. Patent Documents, change "2005/0222618 A1* 10/2005 Dreyfuss" to --2005/0222618 A1* 10/2005 Dreyfuss et al.--

In the Drawings

Sheet 1, replace Fig. 2 with the attached Fig. 2

Signed and Sealed this
Thirteenth Day of November, 2018

Andrei Iancu
*Director of the United States Patent and Trademark Office*

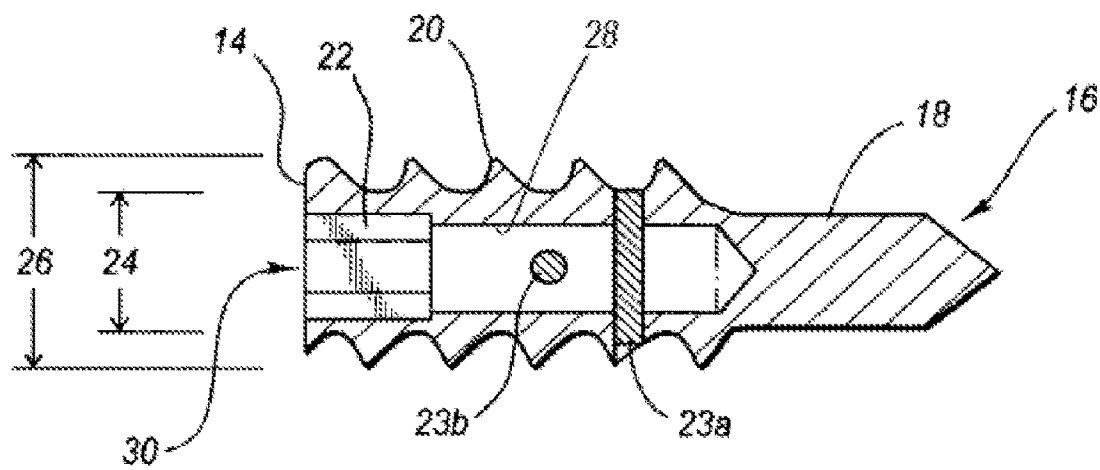
Fig. 2